United States Patent [19]

Schaefer

[11] 4,429,096

[45] Jan. 31, 1984

[54] QUATERNARY AMINE CARBAMATE OR UREA COMPOUNDS BASED ON ISOPROPENYL-α,α-DIMETHYLBENZYL ISOCYANATE

[75] Inventor: Frederic C. Schaefer, Darien, Conn.

[73] Assignee: American Cyanamid Company, Stamford, Conn.

[21] Appl. No.: 500,068

[22] Filed: Jun. 1, 1983

[51] Int. Cl.³ .................. C08F 212/14; C08F 220/56
[52] U.S. Cl. ................................. 526/287; 526/301; 526/302; 526/312; 526/307.3; 560/33; 564/48; 260/459 R
[58] Field of Search ............... 526/287, 301, 302, 312, 526/307.3; 564/48; 560/33; 260/459 R

[56] References Cited

U.S. PATENT DOCUMENTS

| | | | |
|---|---|---|---|
| 2,492,332 | 12/1949 | Sayigh et al. | 560/33 |
| 2,606,892 | 8/1952 | Kropa | 526/310 |
| 2,673,878 | 3/1954 | Cusic | 564/48 |
| 2,762,842 | 9/1956 | Hafliger et al. | 564/48 |
| 3,290,350 | 12/1966 | Hoover | 526/312 |
| 3,424,730 | 1/1969 | Lee | 526/312 |
| 3,551,390 | 12/1970 | Kreian | 526/310 |

Primary Examiner—Joseph L. Schofer
Assistant Examiner—Peter F. Kulkosky
Attorney, Agent, or Firm—Steven J. Hultquist

[57] ABSTRACT

A meta- or para-compound of the formula:

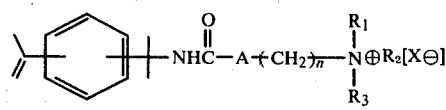

wherein:
X⊖ is an anion selected from the group consisting of $R_4OSO_3\ominus$, $Cl\ominus$, $Br\ominus$ and $I\ominus$;
A is -O- or

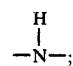

wherein:
n is 2 or 3;
$R_1$, $R_2$ and $R_3$ which may be the same or different, are lower alkyl; and
$R_4$ is lower alkyl or allyl.

Also disclosed is a method of making the compound by reacting meta- or para-isopropenyl-α,α-dimethylbenzyl isocyanate with either an amino alcohol or a dialkylaminoethyleneamine, and quaternizing the reaction product with an alkylating agent. The compound may be polymerized with a co-monomer such as acrylamide to yield water-soluble cationic polymers for use in water clarification, flocculation, and hair spray applications.

8 Claims, No Drawings

QUATERNARY AMINE CARBAMATE OR UREA COMPOUNDS BASED ON ISOPROPENYL-α,α-DIMETHYLBENZYL ISOCYANATE

This invention relates to a meta or a para compound of the formula

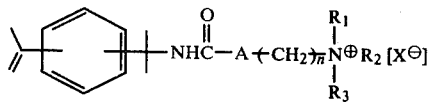

wherein:
$X^{\ominus}$ is an anion selected from the groupc consisting of $R_4OSO_3^{\ominus}$, $Cl^{\ominus}$, $Br^{\ominus}$ and $I^{\ominus}$;
A is —O— or

wherein:
n is 2 or 3; and
$R_1$, $R_2$ and $R_3$ which may be the same or different, are lower alkyl; $R_4$ is lower alkyl and allyl.

In another aspect, the invention relates to a method of making a compound of the formula;

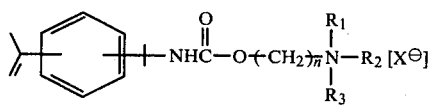

wherein $S^-$, n and $R_1$–$R_3$ are as defined above, comprising:

(a) reacting a meta- or para-monoene-monoisocyanate of the formula

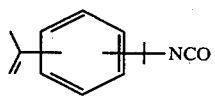

with an amino alcohol selected from the group consisting of dimethylaminoethanol, diethylaminoethanol, dimethylaminopropanol, diethylaminopropanol, and 2-dimethylamino-isobutanol to yield a tertiary amino-carbamate of the formula:

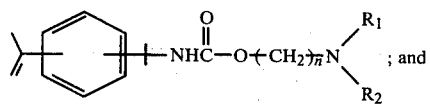

(b) quaternizing said tertiary amino-carbamate, with an alkylating agent selected from the group consisting of dimethylsulfate, methyl chloride, allyl chloride, ethylene oxide and epichlorohydrin, to yield said compound.

In a still further aspect, the invention relates to a method of making a meta- or para-compound of the formula:

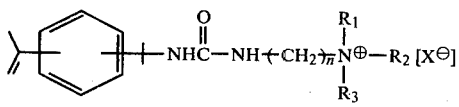

wherein $X^{\ominus}$, n and $R_1$–$R_3$ are as previously defined, comprising:

(a) reacting a meta- or para-monoene-monoisocyanate of the formula:

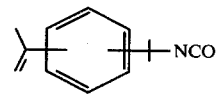

with a dialkylaminoalkyleneamine of the formula:

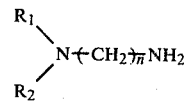

to yield a tertiary amino-urea of the formula

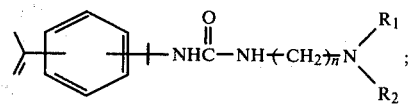

and (b) quaternizing said tertiary amino-urea, with an alkylating agent selected from the group consisting of dimethyls fulate, methyl chloride, allyl chloride, ethylene oxide and epichlorohydrin, to yield said compound In an additional aspect of the invention, the compounds of the formula:

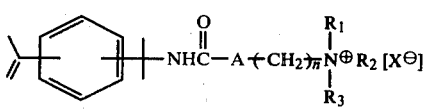

suitably may be co-polymerized under polymerization conditions with acrylamide to form a copolymer which is water-soluble and has utility in water clarification, flocculation and hair sprays, as a cationic copolymer.

The cationic structure of the compound of the invention renders the same water-soluble and compatible with comonomers such as acrylamide, as mentioned. The cationic moiety therein provides substantivity of copolymers based thereon to anionic substrates.

The polymerizable isopropenyl phenyl moiety of the compound of the instant invention affords copolymerization characteristics which are different from conventional cationic monomers, which facilitate advantageous copolymer compositions. Specifically, the cationic carbamate structure can be eliminated thermally to regenerate isocyanate and/or olefin structures which are water-repellant in character and reaction toward cellulose, as shown by the reaction sequence below

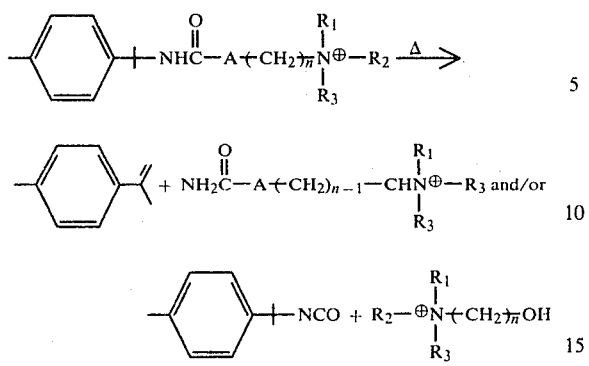

In making the quaternary amino-carbamate compound of the invention, the olefinic isocyanate (TMI) is suitably reacted with an amino alcohol such as dimethylaminoethanol to give a tertiary amino-carbamate which is then quaternized with dimethylsulfate or a similar alkylating agent.

Other amino alcohols which may be used in place of dimethylaminoethanol in practicing the present invention include diethylaminoethanol, dimethylaminopropanol, diethylaminopropanol, and 2-dimethylaminoisobutanol.

The tertiary amino-carbamate can be quaternized with methyl chloride, allyl chloride and the like, or with epoxides such as ethylene oxides or epichlorohydrin.

Tertiary amino- and quaternary ammonio-ureas can be prepared for similar end-use applications by reaction of the meta- or para-substituted isocyanate with appropriate amines such as dimethylaminoethyleneamine and diethylaminopropyleneamine.

Alternatively, quaternary ammonio-alcohols or amines can be reacted with the isocyanates to give the compounds of the present invention in one step.

The invention is more fully illustrated by the following examples, wherein all parts and percentages are by weight unless otherwise indicated.

EXAMPLE I 87 grams (0.43 mole) of para-isopropenyl-α,α-dimethylbenzyl isocyanate (TMI) was mixed with 38 grams (0.43 mole) of dimethylaminoethanol. A mildly exothermic reaction occurred leading to partial crystallization. After one hour, the mixture was additionally heated for two hours on the steam bath to give substantially complete conversion of the isocyanate to the tertiary-amino carbamate. The reaction product was then diluted with 150 cc of hexane, and the solution was filtered to remove 2.2 grams of byproduct urea derivative.

To the hexane solution was gradually added 0.43 mole of methyl sulfate (55 g., 98% pure) over a period of 15 minutes. Reaction was exothermic and was held at the boiling point of the hexane solvent. The viscosity gradually increased, and the mixture became opaque as the quaternary salt separated. The hexane-insoluble product was extracted twice with fresh hexane in 150 cc portions and was also extracted with ethyl ether to remove a little isocyanate and other organic impurities. The residual syrup was dissolved in 130 cc of water, and the solution was filtered to remove a small amount of additional urea derivative (produced by hydrolysis of residual isocyanate). The clarified solution weighed 290 g. The solids content was found to be 50.1% by evaporation at 90° under vacuum; the residue was a hard gum at room temperature. Analysis by titration with tetraphenylborate indicated the quaternary salt content of the solution to be 57.0%. Measurement of unsaturation by bromination gave a value of 56.9%.

EXAMPLE II

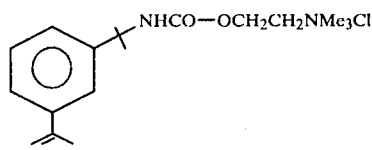

A mixture of m-TMI (38 g. of 97% purity, 0.19 mole), 27.9 g. (0.20 mole) of anhydrous choline chloride, and 6 drops of dibutyltin dilaurate was heated at reflux for two hours. A clear solution was obtained in about one hour. The product carbamate crystallized as the solution cooled. Filtration and washing with fresh acetonitrile gave slightly impure material in approximately 95% yield. This was recrystallized from acetonitrile to give m.p. 192°–195°. The $^{13}$C-NMR spectrum was consistent with the structure of 2-[N-(m-isopropenyl-α,α-dimethylbenzyl) carbamoyloxy]ethyltrimethylammonium chloride

EXAMPLE III

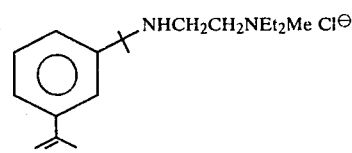

N, N-Diethylethylenediamine (0.25 mole) is added dropwise at 25°–30° C. to 0.25 mole of m-TMI dissolved in 125 g. of acetonitrile. After 30 minutes the solution is transferred to a 300 μ rocking autoclave and 0.3 mole of methylchloride is introduced. The autoclave temperature is raised to 100° C. in one hour and then is allowed to cool. The quaternary salt is recovered by evaporation of the product solution to dryness.

EXAMPLE IV

Acrylamide was dissolved in a 35% solution of the cationic monomer of Example I to give a 90/10 molar ratio of acrylamide/cationic monomer Wako-50 catalyst (4000 ppm) gave complete conversion in 24–48 hours at 50° C. The standard viscosity obtained was 1.45 cps.

Co-application of this copolymer solution with glyoxal increases the wet strength of paper.

What is claimed is:

1. A meta- or para-compound of the formula;

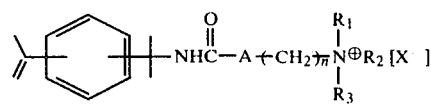

wherein:
X⁻ is an anion selected from the group consisting of R₄OSO₃⊖, Cl⊖, Br⊖ and I⊖;
A is —O— or

wherein:
n is 2 or 3;
$R_1$, $R_2$ and $R_3$ which may be the same or different, are lower alkyl; and $R_4$ is lower alkyl or allyl.

2. A compound according to claim 1 wherein $R_1$, $R_2$, $R_3$ and $R_4$ are methyl.

3. A compound according to claim 2 wherein n is 2 and A is —O—.

4. A method of making a compound of the formula

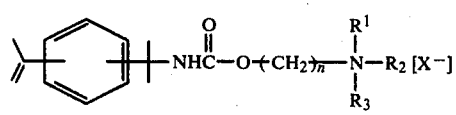

wherein:
$X^-$ is an anion selected from the group consisting of $R_4OSO_3^\ominus$, $Cl^\ominus$, $Br^\ominus$ and $I^\ominus$;
wherein:
n is 2 or 3;
$R_1$, $R_2$, $R_3$, which may be the same or different, are lower alkyl; and
$R_4$ is lower alkyl or allyl, comprising:
(a) reacting ameta- or para-monoene-monoisocyanate of the formula:

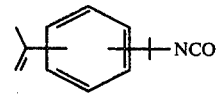

with an amino alcohol selected from the group consisting of dimethylaminoethano, diethylaminoethanol, dimethylaminopropanol, diethylaminopropanol, and 2-dimethylaminoisobutanol to yield a tertiary amino-carbamate of the formula:

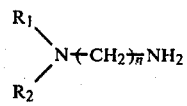; and (b) quaternizing said tertiary amino-carbamate, with an alkylating agent selected from the group consisting of dimethylsulfate, methyl chloride, allyl chloride, ethylene oxide and epichlorohydrin, to yield said compound.

5. A method according to claim 4 wherein n is 2, and $R_1$, $R_2$, $R_3$ and $R_4$ are methyl.

6. A method of making a meta- or para-compound of the formula:

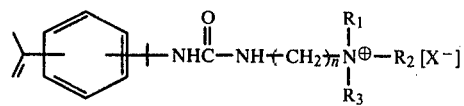

wherein: $X^-$ is an anion selected from the group consisting of $R_4OSO_3^\ominus$, $Cl^\ominus$, $Br^\ominus$, and $I^\ominus$
wherein: $R_1$, $R_2$ and $R_3$, which may be the same or different, are lower alkyl; and $R_4$ is lower alkyl or allyl, comprising:
(a) reacting a meta- or para-monoene-monoisocyanate of the formula

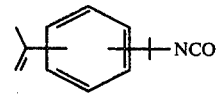

with a dialkylaminoalkyleneamine of the formula

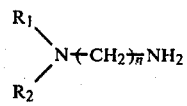

to yield a tertiary amino-urea of the formula:

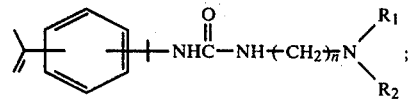

and
(b) quaternizing said tertiary amino-urea, with an alkylating agent selected from the group consisting of dimethyl sulfate, methyl chloride, allyl chloride, ethylene oxide and epichlorohydrin, to yield said compound.

7. A method of making a compound according to claim 1 comprising reacting the corresponding quaternary amino-alcohol or amine with a meta- or para-monoene-monoisocyanate of the formula

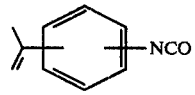

8. A copolymer of the compound of claim 1 and acrylamide.

* * * * *